(12) United States Patent
Gao

(10) Patent No.: US 11,293,839 B2
(45) Date of Patent: Apr. 5, 2022

(54) DEVICE FOR FECAL SAMPLE COLLECTION AND EXTRACTION

(71) Applicant: Ping Gao, San Diego, CA (US)

(72) Inventor: Ping Gao, San Diego, CA (US)

(73) Assignee: Epitope Biotechnology Co., Ltd., Jiaxing (CN)

( * ) Notice: Subject to any disclaimer, the term of this patent is extended or adjusted under 35 U.S.C. 154(b) by 729 days.

(21) Appl. No.: 16/104,119

(22) Filed: Aug. 16, 2018

(65) Prior Publication Data

US 2020/0056965 A1 Feb. 20, 2020

(51) Int. Cl.
| | | |
|---|---|---|
| *G01N 1/02* | (2006.01) | |
| *B01L 3/00* | (2006.01) | |
| *G01N 1/38* | (2006.01) | |
| *A61B 10/00* | (2006.01) | |

(52) U.S. Cl.
CPC ........... *G01N 1/02* (2013.01); *A61B 10/0038* (2013.01); *B01L 3/508* (2013.01); *G01N 1/38* (2013.01); *B01L 2200/0689* (2013.01); *B01L 2300/042* (2013.01); *B01L 2300/0832* (2013.01); *G01N 2001/383* (2013.01)

(58) Field of Classification Search
CPC ...... G01N 1/02; G01N 1/38; G01N 2001/383; G01N 1/10; A61B 10/0038; A61B 10/0096; B01L 3/508; B01L 2200/0689; B01L 2300/042; B01L 2300/0832
See application file for complete search history.

(56) References Cited

U.S. PATENT DOCUMENTS

| | | |
|---|---|---|
| 4,539,180 A | 9/1985 | Schwartz |
| 4,770,853 A | 9/1988 | Bernstein |
| 4,844,818 A | 7/1989 | Smith |
| 4,943,522 A | 7/1990 | Eisinger et al. |
| 4,978,504 A | 12/1990 | Nason |
| 5,198,365 A | 3/1993 | Grow et al. |
| 5,250,412 A | 10/1993 | Giegel |
| 5,275,785 A | 1/1994 | May et al. |

(Continued)

FOREIGN PATENT DOCUMENTS

| | | | | |
|---|---|---|---|---|
| CN | 102564796 A | * | 7/2012 | ............ B01L 3/5023 |
| DE | 10205709 A1 | | 8/2003 | |

(Continued)

OTHER PUBLICATIONS

Washington Dept of Health, "Instructions for the Fecal Occult Blood Test" captured on Jan. 20, 2015 by wayback machine, pp. 1-2. (Year: 2015).*

(Continued)

*Primary Examiner* — Dennis White
(74) *Attorney, Agent, or Firm* — Wagenknecht IP Law Group PC

(57) ABSTRACT

Provided is a simple and easy to operate device for collecting and extracting fecal samples. The collection device of the invention comprises a top cap mounted with a sample collection means, a middle cap inserted with an elastic sealing funnel, and a bottom container having only one opening. The device can collect fecal samples with a quantitative sampling accuracy comparable to that of the conventional weighing method. It can also be easily adapted to automated multi-sample extraction and immunoassays.

14 Claims, 5 Drawing Sheets

(56) References Cited

U.S. PATENT DOCUMENTS

| | | |
|---|---|---|
| 5,415,994 A | 5/1995 | Imrich et al. |
| 5,514,341 A * | 5/1996 | Urata ............... A61B 10/0038 422/534 |
| 5,602,040 A | 2/1997 | May et al. |
| 5,622,871 A | 4/1997 | May et al. |
| 5,654,162 A | 8/1997 | Guire et al. |
| 5,656,503 A | 8/1997 | May et al. |
| 5,658,531 A | 8/1997 | Cope et al. |
| 5,714,389 A | 2/1998 | Charlton et al. |
| 5,869,003 A | 2/1999 | Nason |
| 5,877,028 A | 3/1999 | Chandler et al. |
| 5,879,635 A | 3/1999 | Nason |
| 5,965,453 A | 10/1999 | Skiffington et al. |
| 5,965,456 A | 10/1999 | Malmqvist et al. |
| 6,020,147 A | 2/2000 | Guire et al. |
| 6,020,150 A | 2/2000 | Contant-Pussard et al. |
| 6,074,606 A | 6/2000 | Sayles |
| 6,156,271 A | 12/2000 | May |
| 6,187,598 B1 | 2/2001 | May et al. |
| 6,228,660 B1 | 5/2001 | May et al. |
| 6,271,046 B1 | 8/2001 | Chandler |
| 6,352,862 B1 | 3/2002 | Davis et al. |
| 6,372,516 B1 | 4/2002 | Sun |
| 6,375,896 B1 | 4/2002 | Wuske et al. |
| 6,485,982 B1 | 11/2002 | Charlton |
| 6,534,320 B2 | 3/2003 | Ching et al. |
| 6,663,833 B1 | 12/2003 | Stave et al. |
| RE38,430 E | 2/2004 | Rosenstein |
| 6,818,455 B2 | 11/2004 | May et al. |
| 6,890,484 B2 | 5/2005 | Bautista et al. |
| 6,924,153 B1 | 8/2005 | Boehringer et al. |
| 7,090,803 B1 | 8/2006 | Gould et al. |
| 7,098,040 B2 | 8/2006 | Kaylor et al. |
| 7,241,417 B2 | 7/2007 | Lee et al. |
| 7,780,915 B2 | 8/2010 | Gao |
| 9,752,967 B2 | 9/2017 | Pavels Petersen et al. |
| 2002/0173047 A1 | 11/2002 | Hudak et al. |
| 2003/0021727 A1 | 1/2003 | Weyker et al. |
| 2005/0106750 A1 | 5/2005 | Tung et al. |
| 2005/0112023 A1 | 5/2005 | Liang |
| 2010/0121046 A1 | 5/2010 | Ahlquist et al. |
| 2011/0244461 A1 | 10/2011 | Tanigami et al. |

FOREIGN PATENT DOCUMENTS

| | | | |
|---|---|---|---|
| DE | 102008057866 A1 | 5/2010 | |
| DE | 102012109457 A1 * | 4/2014 | ......... A61B 10/0038 |
| DE | 102012022135 A1 | 5/2014 | |
| EP | 0766973 A1 | 4/1997 | |
| EP | 2617362 B1 | 4/2019 | |
| WO | WO-03068398 A1 * | 8/2003 | ......... A61B 10/0038 |
| WO | 2009/136445 A1 | 11/2009 | |
| WO | 2018/234566 A1 | 12/2018 | |
| WO | 2019/023218 A1 | 1/2019 | |
| WO | 2019/215199 A1 | 11/2019 | |

OTHER PUBLICATIONS

EP19191908.3 Extended European Search Report dated Nov. 11, 2019.

PCT/US2018/043465 International Search Report and Written Opinion dated Oct. 2, 2018.

* cited by examiner

DEVICE FOR FECAL SAMPLE COLLECTION AND EXTRACTION

BACKGROUND OF THE INVENTION

Field of the Invention

The present invention relates to a fecal sample collection and extraction device, to be used in immunological tests, for determination of one or more analytes, such as calprotectin, *Helicobacter pylori* and the like.

Description of the Related Art

Like blood and urine, feces are invaluable specimens to be used in clinical diagnostic tests, especially for gastrointestinal diseases. Two common methods used for testing analytes in fecal samples are the chemical method, in which an analyte in the fecal sample reacts with an chemical reagent to generate a chromogenic product indicative of the presence of the analyte of interest, and the immunological method, in which specific antibody for the analyte of interest is used to capture the analyte in the fecal sample and gives rise to a colored/fluorescent/luminescent signal once the analyte is bound to the specific antibody. The immunological method is the preferred choice since it has much higher specificity and sensitivity than that of the chemical method. For both analytical methods, it is important to collect defined amount of fecal samples from patients before the analysis can be performed.

A conventional sampling method is to manually collect a fecal sample and weigh it on an analytic scale. The weighing method is time-consuming, unpleasant to use, and label-intensive for operating a large amount of samples. However, it can collect fecal samples with accurate measurements of the sample weight, resulting in accurate sample extraction with an accurate dilution factor. The weighing method, although hard to operate, is still the most commonly used sample collection method for quantitative analysis of fecal samples due to its high sampling accuracy.

Another sampling method uses a collection stick with a brush-like or grooved structure for collecting feces, which is inserted into a through-hole to remove excessive feces (U.S. Pat. No. 5,882,942 and European Patent No. 1366715). The sampling device, as shown in FIG. 5, comprises a main container housing an extraction solution, an opening portion at the lower end of the main container, a cap placed on the upper end of the main container, a collecting stick mounted on the cap, a separating means held in the main container, and a through-hole formed in the separating means to accommodate the collecting stick through it, wherein the forward end of the collecting stick has grooves or radically extended hairs. Using the through-hole to remove excessive feces, this sampling device can collect approximately constant amount of fecal samples, but the sampling accuracy is not as high as that of the weighing method. These methods are often used in qualitative immunochromatographic test. None of these methods can achieve the sampling accuracy required for quantitative immunologic analysis such as ELISA (enzyme-linked immunosorbent assay). Another disadvantage of the methods is that the separating means is fixed on one end of the main container for engaging the collecting stick mounted on the upper cap, while the other end of the main container has an opening or dripping portion for accessing the extracted fecal sample. Thus, the main container has two opening ends. Since the suspension and the extraction of fecal samples often involves vigorous shaking or vortexing, the two opening ends, especially the lower end opening, can lead to leakage during the operation.

In the sampling device of EP1366715 (FIG. 5a), it uses a screw cap at the lower end of the main container. After sample extraction, the extracted solution can be retrieved from the lower end opening. However, during vigorous shaking or vortexing, the fecal extraction solution may be leaking out from the screw cap either due to careless operation or imperfect sealing caps, which leads to loss of testing materials and contamination of the environment. A centrifugation step is often needed to separate insoluble fecal substances from the soluble extract after the extraction process. Since the device uses the lower opening for retrieving the extraction solutions, the device needs to be upside down during the centrifugation and the solution retrieval, which puts a lot of pressure on the seal between the collection stick and the separation means of the collection device. The breakage or leakage of this seal can lead to loss of extraction solution and excessive extraction from the feces in the cavity of separation means.

For the fecal sampling device of U.S. Pat. No. 5,882,942 (FIG. 5b), it uses a brush or brush-like structure for fecal sample collection, which is claimed to facilitate collection of occult blood on the surface of feces. A disadvantage of the brush or brush-like structures is the difficulty to make each brush hold the exact same volume of fecal samples required for quantitative extraction and analysis. At best, it can be used to extract "approximately constant amount of feces" as described in the patent. Another disadvantage is the dripping portion equipped at the lower end of the device, which is fragile and easy to be broken during the vigorous extraction procedure. The dripping portion is used to deliver extraction solution drops, which is convenient for use in immunological strip tests. However, it is not easy to be used for plate-based ELISAs or magnetic bead based chemiluminescent immunoassays that require accurate and quantitative retrieval of the fecal extraction solution.

The present invention provides an easy-to-operate fecal collection device that has only one opening end and can achieve the quantitative sampling with an accuracy as high as that of the weighing method.

SUMMARY OF THE INVENTION

The present invention pertains to methods and devices for convenient fecal sample collection and quantitative sample extraction. It is an objective of the present invention to provide a device for easily collecting fecal samples with constant sampling volumes that can achieve quantitative accuracy as high as that of the weighing method. It is another objective of the present invention to provide a leakage-proof fecal sample collection device with one opening both for receiving the fecal sample and retrieving/accessing the fecal extraction solution. The present invention solves the leakage problem that often occurs in a fecal collection device with two openings, one for receiving the fecal sample and the other for retrieving the extraction solution. It is another objective of the present invention to provide a fecal sample collection and extraction device with the flexibility to be used for a variety of immunological tests including strip-based rapid tests, plate-based ELISAs, and other chemiluminescent immunoassay on automatic immunology analyzers. It is especially easy to be adapted to most automated shaking/vortexing machines and immunology analyzers. The present invention uses the specially designed middle and top caps having the sampling wand and the sealing funnel for convenient fecal sample collection and quantitative sample extraction, while the bottom container can be any form of test tubes/containers, standard or nonstandard, that can be shaped to fit with any automated shaking machine and/or immunology analyzer.

In one embodiment, the present invention provides a device for fecal sample collection and extraction comprising: a bottom container for housing an extraction buffer, hollow on the inside with one opening on the top; a middle cap provided with a top part to be sealably applied to a top cap, an elastic sealing funnel, a bottom part (O-ring structure) to be sealably applied to the bottom container, and an annular seal inside the bottom part to abut sealably on the top end of the bottom container; and a top cap provided with a cap portion to be sealably applied to the middle cap, which is mounted with a sampling wand for collecting feces samples, wherein the sampling wand protrudes into the bottom container by passing through the sealing funnel when the top cap is applied onto the middle cap and the middle cap is applied onto the bottom container. When the sampling wand is pushed through the narrow stem of the elastic sealing funnel, the sealing funnel forms a tight seal with the sampling wand, ensuring that the exact volume of feces sample contained in the grooves of the sampling wand is used for sample extraction and the extraction buffer is prevented from entering the sealing funnel.

In one embodiment of the present invention, the sealing funnel, made of elastic materials, comprises a wide mouth and a narrow stem portion, wherein the narrow stem has a substantially cylindrical shape having an inner diameter no bigger than the outer diameter of the sampling wand so as to allow forming a tight seal between the cylindrical stem and the sampling wand when the sampling wand is pushed through the sealing funnel. The vertical length of the cylindrical stem of the sealing funnel is 0.8 to 15 mm, preferably 2 to 5 mm.

In one embodiment of the present invention, the sampling wand has a substantially cylindrical rod shape with spiral grooves at its forward end for collecting fecal samples. The external shape of the grooved region of the sampling wand is also cylindrical.

In one embodiment of the present invention, the bottom container is shaped to fit into sample holders of automatic extraction machines for multi-sample extraction and automated immunology multi-analyzer.

In one embodiment of the present invention, the middle cap comprises a bottom part having an inner thread able to sealably engage an external thread provided on the top part of the bottom container.

In one embodiment of the present invention, the middle cap comprises a top part having an external thread able to sealably engage an inner thread provided in the cap portion of the top cap.

In one embodiment of the present invention, the volume of feces sample contained in the grooves of the sampling wand is 5 to 100 μl, preferably 5-20 μl.

In one embodiment of the present invention, the inter-device variation of sample volumes contained in the grooves of the sampling wands is less than 15%, preferably less than 5%.

In one embodiment of the present invention, the feces and the extraction buffer is mixed with a dilution factor of 1:100 to 1:1600, preferably 1:300 to 1:800.

In one embodiment, the present invention provides a method of using the invented device to collect and extract a fecal sample, comprising: a) dipping the sampling wand into multiple sites of feces to collect the fecal sample; b) slowly inserting the sampling wand through the sealing funnel into the extraction buffer in the bottom container and sealing the top cap onto the middle cap; c) vortexing or shaking the device to extract the fecal sample using the extraction buffer; and d) unscrewing the middle cap from the bottom container and taking the feces extract for subsequent assays.

In one embodiment of the present invention, the feces extract is directly applied in an analytic assay selected from a group consisting of fecal calprotectin assay, fecal occult blood assay, fecal *Helicobacter pylori* antigen assay, fecal rotavirus antigen assay, and fecal *Giardia lamblia* antigen assay.

DETAILED DESCRIPTION

Figure 1:
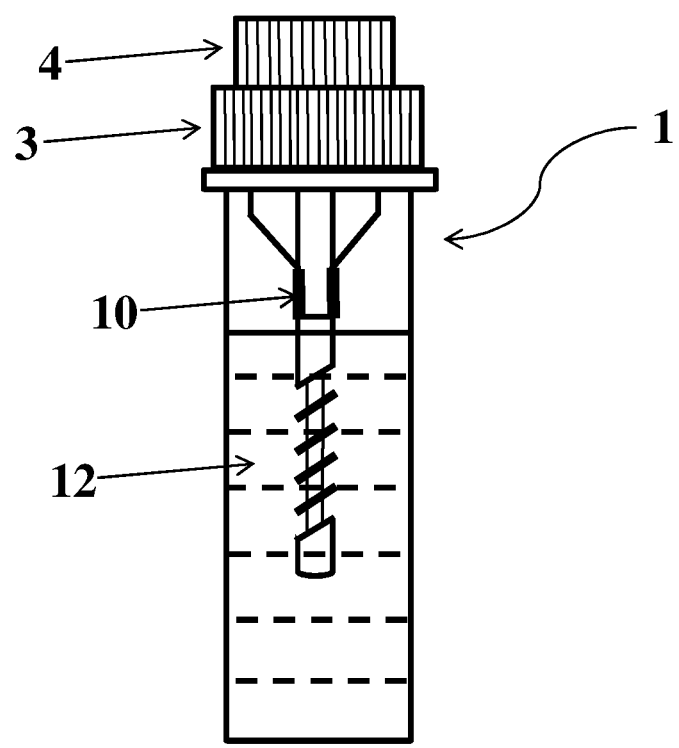
FIG. 1 shows a front view of an exemplary fecal sample collection and extraction device of the present invention in a closed format. The device (1) comprises a top cap (4), a middle cap (3) and a bottom container (2).

The present invention provides a device for convenient fecal sample collection and quantitative sample extraction. The fecal sample collection and extraction device of the present invention comprises a top cap mounted with a sample sampling wand, a middle cap inserted with a sealing funnel, and a bottom container. The device uses an elastic sealing funnel that forms a tight seal with the sampling wand when the wand is inserted through the sealing funnel to ensure that the constant amount of feces filled in the grooves of the sampling wand is used for sample extraction. It provides a quantitative fecal sampling method that can reach the sampling accuracy on a par with that of the conventional weighing method. Another advantage of the invented device is that the sealing funnel is held on the middle cap instead of the bottom container, which allows the bottom container to use one opening for both receiving the fecal sample and retrieving the extraction solution. This eliminates the problem that solution may be leaked from the second opening of the fecal collection tubes of the prior art that have two openings. With only one opening, the bottom containers can also take any standard or non-standard form of test tubes/containers that fit in any automatic shaking machine and immunology analyzer. This enables multiple fecal samples to be simultaneously extracted on a shaking machine and subsequently tested on an automated immunology analyzer even without transferring the extraction solution, which greatly simplifies the testing procedure and minimizes human operation errors.

The advantageous features of the invented device can be further illustrated in the following preferred embodiment referring to the drawings.

Figure 2:
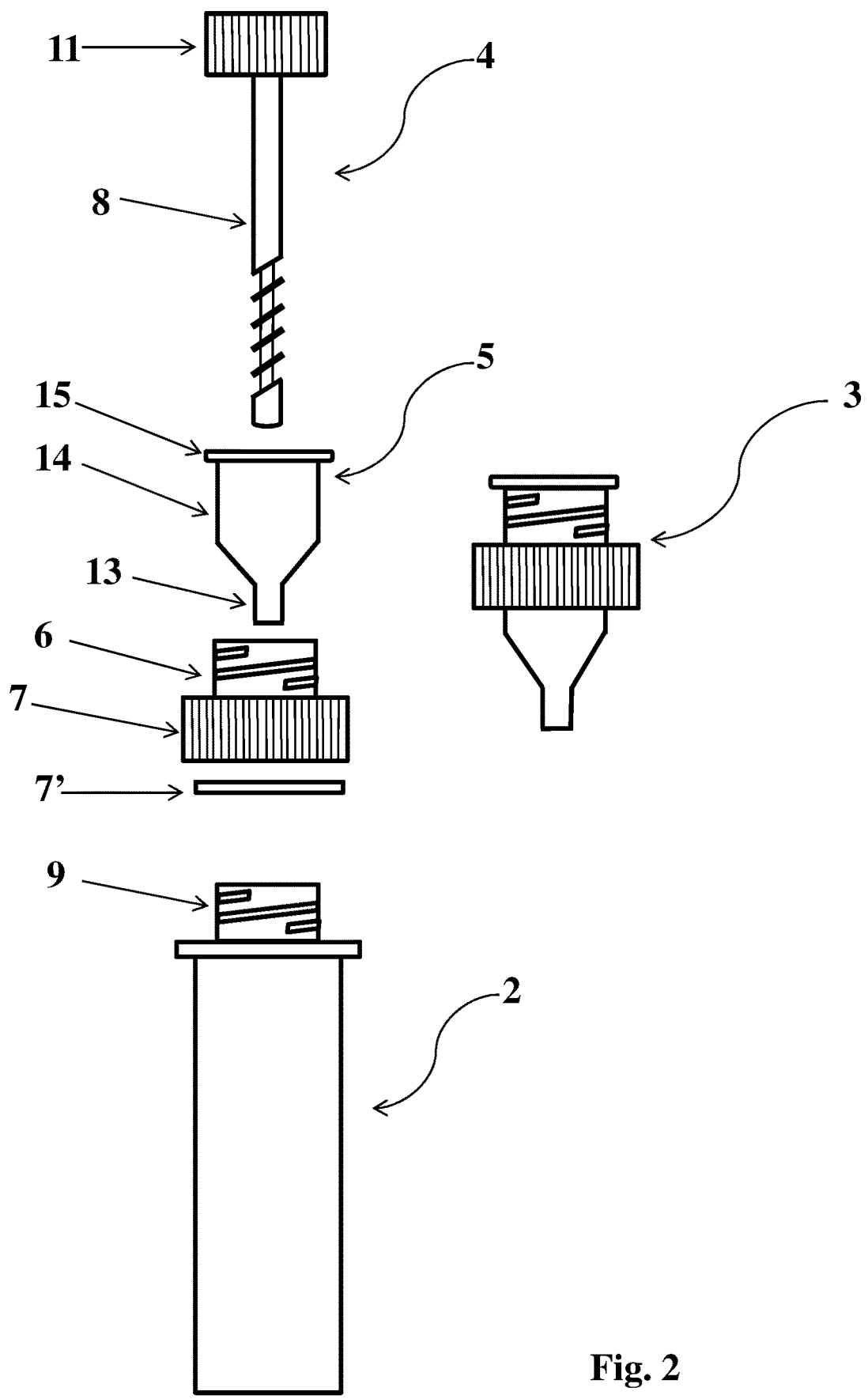
FIG. 2 shows a diagrammatic view of the components of an exemplary device of the present invention. The three major components of the device are a top cap (4) having a cap portion (11) and mounted with a sampling wand (8); a middle cap (3) having a top part (6) with an external thread, a bottom part with an inner thread, an annular seal (7') and a sealing funnel inserted through the middle cap; and a bottom container (2) having a top portion (9) with an external thread and an inner cavity for holding extraction solution.

The present invention provides a device for fecal sample collection and extraction, as shown in FIGS. 1 and 2, comprising: a bottom container (2) for housing an extraction buffer (12), hollow on the inside with one opening on the top (9); a middle cap (3) provided with a top part (6) to be sealably applied to a top cap (4), a sealing funnel (5), a bottom part (7) to be sealably applied to the bottom container, and an annular seal (7') inside the bottom part to abut sealably on the top end of the bottom container; and the top cap (4) provided with a cap portion (11) to be sealably applied to the middle cap (3), which is mounted with a sampling wand (8) for collecting feces samples, wherein the sampling wand protrudes into the bottom container by passing through the sealing funnel when the top cap is applied onto the middle cap and the middle cap is applied onto the bottom container. When the sampling wand is pushed through the sealing funnel, the sealing funnel forms a seal (10) with the sampling wand and removes extra feces on the sampling wand to ensure that the exact same volume of feces sample filled the grooves of the sampling wand is used for sample extraction.

The bottom container (2) of the invention comprises a internal cavity for housing the extraction solution (12) and one opening that can be sealably applied to the middle cap (3). The bottom container can be made of solid materials, preferably transparent materials, such as plastic and glass. There is no limitation regarding the shape of the bottom container. Preferably, it can be a standard test tube that can be conveniently used for shaking and vortexing. It can also be shaped to fit into sample holders of any automatic shaking or vortex machines and/or those of immunology analyzers for multi-sample analysis. Preferably, the same test tube can fit into sample holders for both the automatic shaking machines and the automated immunology analyzers. In this way, the same collection and extraction device can be directly used in both equipment without solution transfer. There is no particular limitation of the volume of the bottom container as long as the upper part of the container can fit to the middle cap. The volume of the bottom container can be, for example, 5 to 500 ml, preferably 10 to 50 ml.

The top cap (4) comprises the cap portion (11) and the sampling wand (8) that is mounted to the center of the inside of the cap portion. The sampling wand has a forward end with grooves used for collecting and holding fecal samples. The cap portion has a means for sealably engaging the middle cap and provides a structure for mounting the sampling wand.

The top cap can be reversibly sealed to the middle cap using any mechanisms known to an ordinary artisan in the field, including, but not limited to, screwing, snapping and plugging. In a preferable embodiment, the top cap can be screw sealed onto the middle cap wherein they have matching screw threads. For example, the top cap has an inner thread that matches to an external thread provided on the top part of the middle cap. Alternatively, the cap portion of the top can have an outer thread that matches to the inner thread provided on the middle cap.

In a preferable embodiment, the sampling wand is a substantially cylindrical rod that has a forward end with spiral grooves used for collecting feces. The external shape of the grooved region of the sampling wand is also cylindrical. The spiral grooves are positioned close to the end of the sampling wand, but not at the exact end. The very end of the sampling wand comprises a solid cylindrical rod. The diameter of the cylinder, including the outer diameter of the grooved region, can be constant throughout the length of the sampling wand. Alternatively, it can taper to be slightly smaller towards the forward end of the wand, which helps to form a tighter seal with the sealing funnel. The sampling wand can have different sizes which have different volumes in terms of the grooved spaces. Preferably, the spiral grooves are evenly spaced and should have the exact same volume of the grooved spaces for each sampling wand of the same size. The volume of the grooved space of the sampling wand can be 5 to 100 μl, preferably 5-20 μl, which determines the volume of fecal sample used for extraction. Different sizes of the groove volumes can be made by varying the width, the depth and/or the number of the grooves. The diameter of the sampling wand can also be changed if needed. For example, a sampling wand with a larger diameter can accommodate deeper grooves than that with a smaller diameter. The sampling wand can be made of any solid materials including, but not limited to, plastics, silicones, porcelains, glasses, and metals. The surface of the sampling wand is preferably made smooth so as to prevent feces from sticking to the surface.

The middle cap (3) is a cap like structure with two major functions. First, it is reversibly connected to the bottom container (2) and the top cap (4). Secondly, it serves as a holding structure for the elastic sealing funnel (5). It comprises a top part (6) and a bottom part (7) that can be sealably applied to the top cap and the bottom container, respectively. Inside the bottom part of the middle cap, there is a annular seal (7') made of elastic materials, e.g. a rubber O-ring, to aid in sealing the middle cap and the bottom container.

The middle cap can be reversibly sealed to the top cap and the bottom container using any mechanisms known to a person with ordinary skill in the field, including, but not limited to, screwing, snapping and plugging. In a preferable embodiment, the middle cap can be screwed onto the bottom container, comprising a bottom part having an inner thread that is able to sealably engage an external thread provided on the top part of the bottom container. The middle cap comprises a means to be screw connected to the top cap, for example, a top part having an external thread that is able to screw into an inner thread provided in the cap portion of the top cap. It also provides a holding structure for the elastic sealing funnel, enabling the elastic sealing funnel to be reversibly engaged in the bottom container and allowing easy removal of the sealing funnel for retrieving extraction solutions.

The sealing funnel (5), made of elastic materials, is used to remove extra feces on the sampling ward so as to ensure that the exact same amount of fecal samples contained in the grooves is used in the extraction process. It is made of materials with good elasticity such as rubber, silicone and elastic plastics. The sealing funnel comprises an outer edge (15), a wide mouth portion (14) and a narrow stem portion (13). The outer edge (15) of the sealing funnel has a diameter slightly bigger than that of the upper part of the middle cap, which allows the sealing funnel to be held on the rim of the top portion of the middle cap when inserted through the middle cap. The wide mouth portion (14) has a substantially cylindrical shape and tapers to the narrow stem. It can also have a cone-like shape and smoothly tapers to the narrow stem. The sealing funnel is inserted through the middle cap with it outer edge hanging over the rim of the upper part of the middle cap. The outer edge of the sealing funnel holds the funnel onto the top of the middle cap. With its elastic nature, it also helps to form a seal when the top cap is screwed onto the middle cap. Preferably, the wide mouth has a cylindrical shape and the outer diameter of the wide mouth is the same as the inner diameter of the upper part of the middle cap so that the sealing funnel can fit securely inside the middle cap with little room for movement.

The narrow stem portion comprises a substantially cylindrical stem having an inner diameter no bigger than the outer diameter of the grooved region on the sampling wand. This allows forming a tight seal between the cylindrical stem and the sampling wand when the sampling wand is pushed through the sealing funnel. The tight seal is very important for ensuring that only feces contained in the grooves of the sampling wand are able to penetrate the sealing funnel to enter the bottom container for use in sample extraction. When the sealing wand is pressed through the narrow stem of the sealing funnel, fecal sample is pushed to fill any available grooved space while extra feces outside the grooved space are cleared from the sampling wand and remained inside the sealing funnel. Additionally, the tight seal prevents the extraction buffer from flowing into the sealing funnel, which ensures that the exact same amount of feces filled in the grooved space is used for extraction in a defined volume of the extraction buffer. This ensures that the dilution factor is the same for each sample extraction. The vertical length of the cylindrical stem of the sealing funnel is 0.8 to 15 mm, preferably 2 to 5 mm.

In a preferred embodiment, the inner diameter of the upper opening of the narrow stem is slightly smaller than the diameter of the sampling wand. When the sampling wand reaches the upper end of the narrow stem, extra force is needed to push the sampling wand to pass through the elastic narrow stem, thus forming a tight seal. The narrow stem can preferably taper to an even narrower end which can provide a tighter seal between the stem and the sampling wand.

Figure 3:
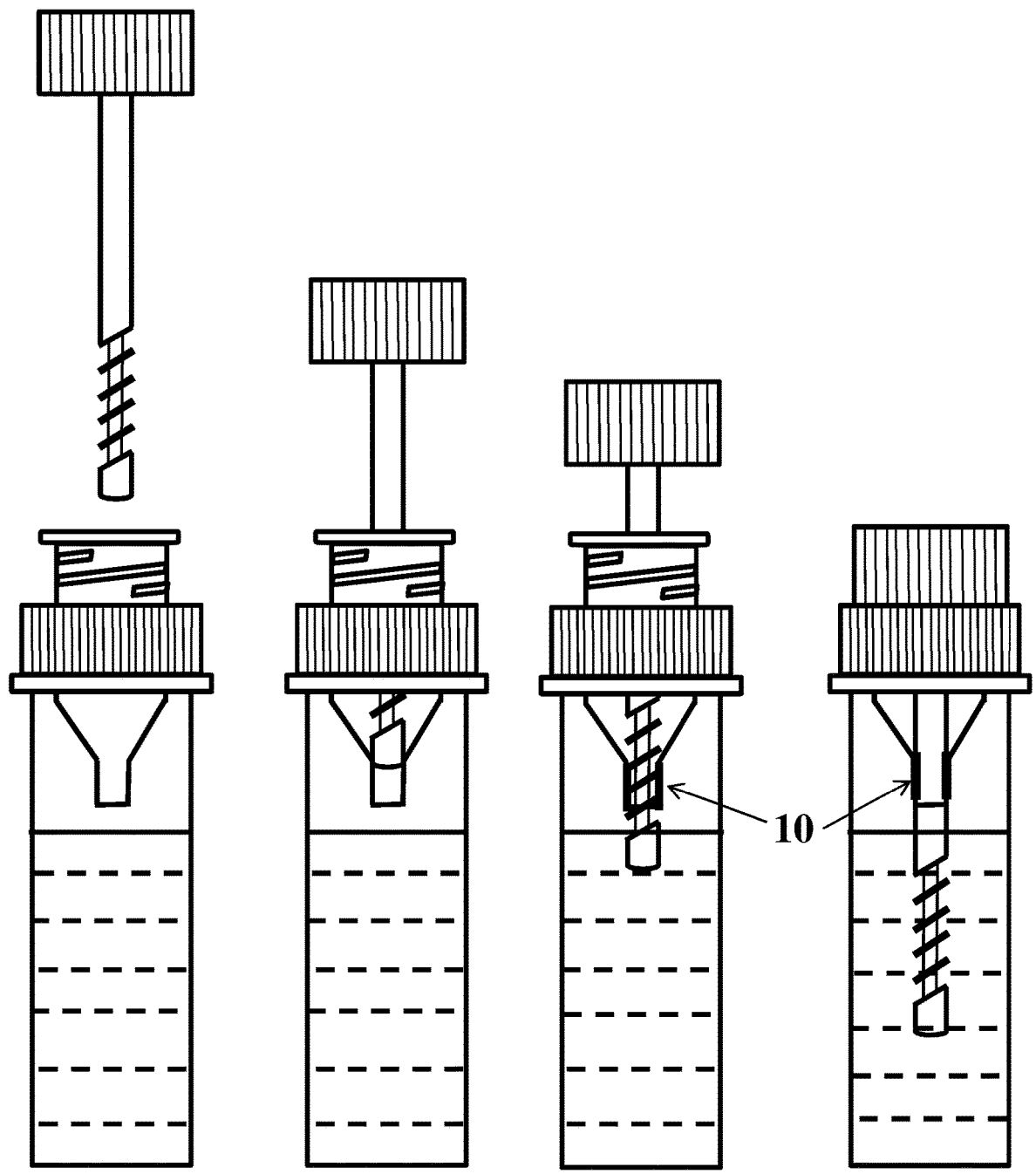
FIG. 3 shows a series of views of inserting the sampling wand into the sealing funnel to form a seal (10) between them.

As shown in FIG. 3, when the sampling wand is forced through the narrow stem of the sealing funnel, the outer edge of the grooved region is pressed by the elastic wall of the narrow stem, which fills feces into the grooved space to its full capacity while keeps feces outside the groove inside the sealing funnel. This ensures that the exact same amount of the feces are retained in the grooved space and are used in the subsequent extraction. Additionally, the tight seal can prevent extraction buffer from entering the sealing funnel. The close interaction between the sampling wand and the sealing funnel provides a mechanism for quantitative fecal sampling that offers a sampling accuracy on a par with that of the conventional weighing method. The method of the invention, however, is much easier and faster to operate than the conventional method.

Figure 4:
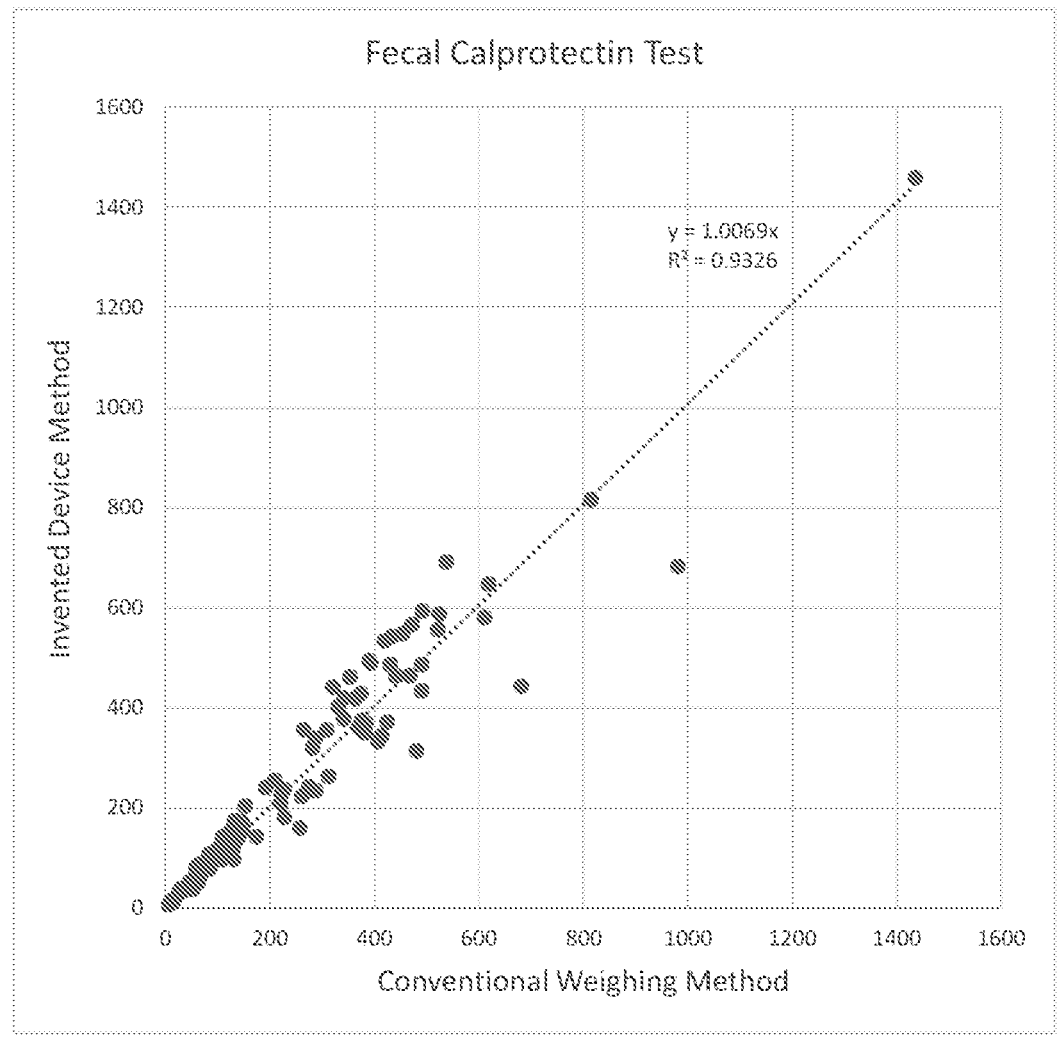
FIG. 4 shows the correlation of measured fecal calprotectin using the conventional weighing method and the invented device.
Figure 5:
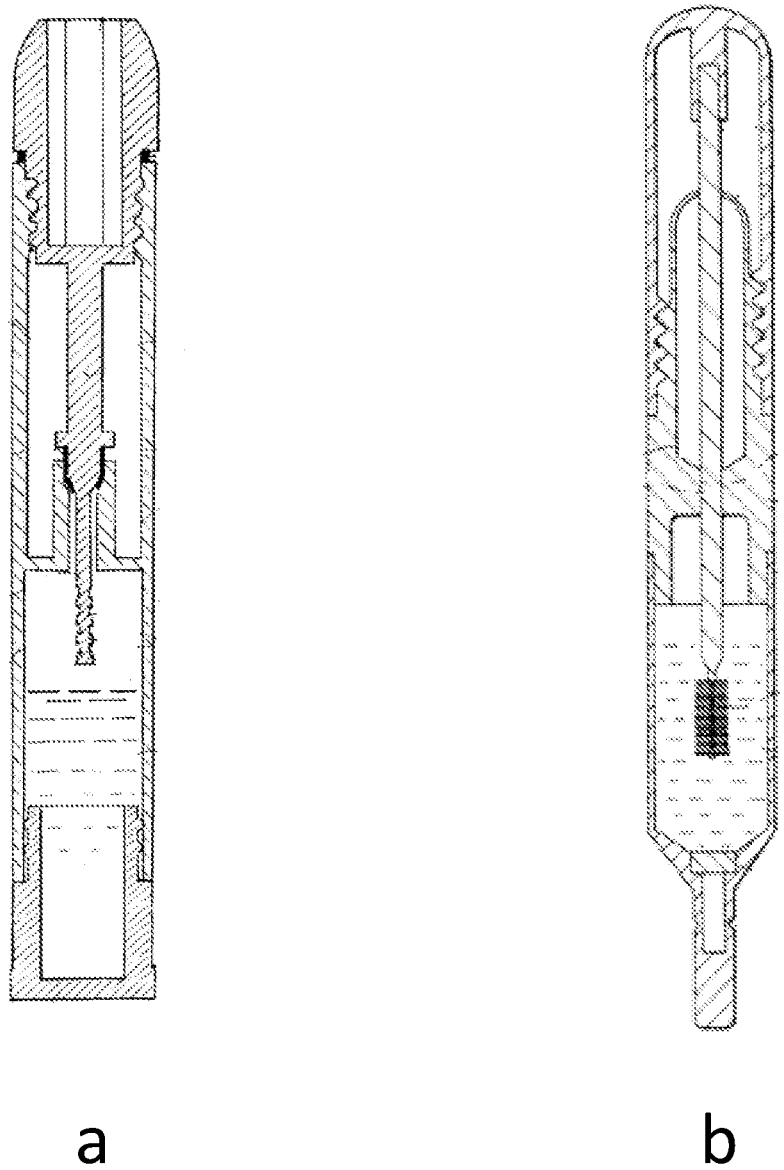
FIG. 5 shows two fecal collection and extraction devices known from the state of art.

When tested in the sample collection experiments using peanut paste as a replacement of feces (see Example 1), the inter-device variation of sample volumes contained in the grooves of the sampling wands is less than 5%. The sampling accuracy is comparable to that of the weighing method. When testing 120 clinical samples with a quantitative fecal calprotectin immunoassay using the conventional weighing method and the invented method for fecal sample collections and extractions (see Example 2), the measured results of calprotectin are highly correlated and the coefficient of determination ($R^2$) of the two methods is as high as 0.93. The linear correlation equation between the measured datasets of the two fecal sample collection methods has a slope 1.006 (FIG. 4), further providing evidence that the datasets from the two methods are highly correlated and comparable to each other.

The present invention provides a method of using the invented device to collect and extract a fecal sample, comprising: a) dipping the sampling wand into multiple sites of feces to collect the fecal sample; b) slowly inserting the sampling wand through the sealing funnel into the extraction buffer in the bottom container and sealing the top cap onto the middle cap; c) vortexing or shaking the device to extract the fecal sample using the extraction buffer; and d) unscrewing the middle cap from the bottom container and taking the feces extract for subsequent assays. When dipping the sample wand into feces, it is important to dip into multiple sites to get a representative sampling of the feces. It is also important to make sure that all the grooved regions is filled with feces, but it is not needed to remove excess feces at this step. The speed of inserting the sampling wand through the sealing funnel should be relatively slow to ensure that all the grooves spaces are evenly filled and excess feces are retained inside the sealing funnel. The grooved region should be completely immersed in the extraction buffer during the extraction process. Depending on the abundance of analytes in the fecal sample, the feces and the extraction buffer can mixed with a volume dilution factor of 1:100 to 1:1600, preferably 1:300 to 1:800. The dilution factor is calculated as dividing the volume of the extraction buffer by the groove volume of the sampling wand. After extraction, the fecal extraction solution may need to be centrifuged to remove insoluble materials before it can be used for subsequent analysis.

This device is especially suitable for use in automated analysis of multiple samples where the bottom container can be selected as any test tubes that fit into multi-tube shakers and automated immunology analyzers. After multiple fecal samples are collected by the invented collection tubes, the collection tubes can be directly loaded onto the multi-tube shakers for extraction and automated analyzer for batch assay testing.

The feces extract obtained from the invented device can be applied in a variety of analytic assays including, but not limited to, fecal calprotectin assay, fecal occult blood assay, fecal *Helicobacter pylori* antigen assay, fecal rotavirus antigen assay, and fecal *Giardia lamblia* antigen assay.

EXAMPLES

Example 1. Evaluation of the Quantitative Consistency of Sample Collection Using the Invented Device To evaluate the quantitative consistency of the fecal sample collection device of the invention, the amount of sample collected in the grooves of the sampling wand of the device was individually measured using a analytical scale. The peanut paste was used as a replacement of fecal samples. The sampling wand was first cut off from the top cap. The cap-less sampling wand was placed on the analytical scale and used to tare the scale to zero. The sampling wand was dipped into multiple sites of the peanut paste to collect a substantial amount of sample, and was pushed to pass through the sealing funnel on the middle cap. The passing-through sampling wand was measured on the analytical scale and the net weight of the sample collected in the grooves was thus obtained.

The measured weight of the collected sample in the grooves was converted to the corresponding volume assuming the density of the peanut paste as 1.059 g/ml. 21 samples were collected and the calculated volumes were shown in the Table 1. The deviation between different sample volumes is only 3.2%.

TABLE 1

Measurements of collected sample volumes using the invented device

| No. | Sample Volume (ul) |
|---|---|
| 1 | 11.43 |
| 2 | 11.52 |
| 3 | 11.99 |
| 4 | 12.18 |
| 5 | 11.33 |
| 6 | 11.52 |
| 7 | 11.33 |
| 8 | 11.61 |
| 9 | 12.65 |
| 10 | 11.71 |
| 11 | 11.33 |
| 12 | 11.05 |
| 13 | 11.71 |
| 14 | 11.33 |
| 15 | 11.33 |
| 16 | 11.80 |
| 17 | 11.99 |
| 18 | 12.09 |
| 19 | 11.80 |
| 20 | 11.80 |
| 21 | 11.43 |
| Average (μl) | 11.7 |
| SD (μl) | 0.37 |
| CV (%) | 3.2 |

Example 2. Measurement of Fecal Calprotecin Using the Invented Device and the Conventional Weighing Method 120 clinical fecal samples were collected and extracted using the conventional weighing method and the invented device. The amount of calprotectin in each sample was determined using an immunoassay specific for calprotectin measurement (Fecal Calprotectin ELISA Kit, Epitope Diagnostics, Inc. San Deigo, Calif.), which utilizes the two-site "sandwich" technique with two selected antibodies that bind to different epitopes of human calprotectin. Briefly, calprotectin protein standards, blank controls and patient sample extractions were added to wells of a microtiter plate coated with a calprotectin antibody. After the first incubation period, the plate was washed and horseradish peroxidase (HRP)-conjugated human calprotectin specific monoclonal antibody was added to each well. After the second incubation period, a "sandwich of solid-phase antibody-human calprotectin-HRP-conjugated monoclonal antibody" was formed. The unbound monoclonal antibodies and buffer matrix were removed in the subsequent washing step. For the detection of this immunocomplex, the well was incubated with a substrate solution in a timed reaction and measured in a spectrophotometric microplate reader. The enzymatic activity of the immunocomplex bound to the wall of each microtiter well is proportional to the amount of human calprotectin in the test sample. A standard curve was generated by plotting the absorbance versus the respective human calprotectin concentration for each standard on a point-to-point or 4-parameter curve fitting. The concentration of fecal human calprotectin in test samples was determined from the standard curve.

The calprotectin in each sample was collected and measured twice using both the invented device and the conventional method. The average calprotectin values for both methods was plotted in FIG. 4. The results from both methods are highly correlated and the coefficient of determination $R^2$ of the two methods is as high as 0.93 with a linear correlation slope at 1.006. This indicates that the sampling accuracy of the invented method is comparable to that of the conventional weighing method.

While the present invention has been described in some detail for purposes of clarity and understanding, one skilled in the art will appreciate that various changes in form and detail can be made without departing from the true scope of the invention. All figures, tables, appendices, patents, patent applications and publications, referred to above, are hereby incorporated by reference.

What is claimed:

1. A device for quantitative collection and extraction of a fecal sample, the device comprising:
   a) a bottom container for housing an extraction buffer, hollow on the inside with one opening on the top;
   b) a middle cap provided with a top part to be sealably applied to a top cap, a bottom part to be sealably applied to the bottom container, and an annular seal inside the bottom part to abut sealably on the top part of the bottom container;
   c) an elastic sealing funnel fitted through said middle cap, said sealing funnel comprising an outer edge held on an upper rim of the top part of said middle cap and a stem with an elastic side wall; and
   d) a top cap provided with a cap portion to be sealably applied to said middle cap by screwing and pressing against said outer edge of said sealing funnel, and a sampling wand having a grooved region for collecting feces samples, said sampling wand protruding into said bottom container by passing through said sealing funnel when said top cap is applied onto the top part of said middle cap and said middle cap is applied onto the top part of said bottom container,
   wherein, when said sampling wand passes through said sealing funnel, said elastic wall stretches to form a tight seal around the grooved region of said sampling wand to ensure that all grooves of said sampling wand are filled to capacity and remaining sample is prevented from passing through said sealing funnel, thereby providing a collected volume of a fecal sample that varies less than 15% from a predetermined volume for quantitative analysis.

2. The device of claim 1, wherein the sampling wand is a substantially cylindrical rod with spiral grooves at its forward end for collection of fecal samples.

3. The device of claim 1, wherein said bottom container is shaped to fit into sample holders of automatic shaking/vortexing machines for multi-sample extraction and/or automated multisample analyzers.

4. The device of claim 1, wherein said middle cap comprises a bottom part having an inner thread able to sealably engage an external thread provided on the top part of said bottom container.

5. The device of claim 1, wherein said middle cap comprises a top part having an external thread able to sealably engage an inner thread provided in the cap portion of said top cap.

6. The device of claim 1, wherein said stem has a length of 0.8 to 15 mm, optionally 2 to 5 mm.

7. The device of claim 1, wherein said stem is a cylindrical column.

8. The device of claim 1, wherein the volume of feces sample contained in the grooves of said sampling wand is 5 to 100 μl, optionally, 5-20 μl.

9. The device of claim 1, wherein the variation is less than 5%.

10. The device of claim 1, wherein the feces and the extraction buffer is mixed with a dilution factor of 1:100 to 1:1600, optionally, 1:300 to 1:800.

11. The device of claim 1, wherein said sealing funnel is formed from silicone.

12. A method of using a device of claim 1 to collect and extract a fecal sample, comprising:
   a) dipping the sampling wand into multiple sites of feces to collect the fecal sample;
   b) slowly inserting the sampling wand through the sealing funnel so that the elastic wall expands around the wand to form a tight seal and ensures the grooves are filled to capacity, then into the extraction buffer in the bottom container and sealing the top cap onto the middle cap afterwards;
   c) vortexing or shaking the device to extract the fecal sample using the extraction buffer; and
   d) unscrewing the middle cap from the bottom container and taking the feces extract for subsequent assays.

13. The method of claim 12, wherein the feces extract is directly applied in an analytic assay selected from a group consisting of fecal calprotectin assay, fecal occult blood assay, fecal *Helicobacter pylori* antigen assay, fecal rotavirus antigen assay, and fecal *Giardia lamblia* antigen assay.

14. A device for quantitative collection and extraction of a fecal sample, the device comprising:
   a) a bottom container for housing an extraction buffer;
   b) a middle cap that connects to said bottom container; and
   c) an elastic sealing funnel fitted through said middle cap, said sealing funnel comprising an outer edge held on an upper rim of said middle cap and a stem with an elastic side wall; and
   d) a top cap sealed to said middle cap by compressing against the outer edge of said sealing funnel, said top cap comprising a sampling wand having a grooved region configured for collecting feces samples, said sampling wand protruding into said bottom container by passing through said sealing funnel, wherein said elastic wall is stretched around said sampling wand to form a tight seal against said grooved region of said sample wand, thereby ensuring that all grooves of said sampling wand are filled to capacity and remaining sample is prevented from passing through said sealing funnel when the grooves are pushed through the stem, further wherein a collected volume of the fecal sample varies less than 5% from a predetermined volume for quantitative analysis.

\* \* \* \* \*